United States Patent
Sharma et al.

(10) Patent No.: US 7,107,098 B2
(45) Date of Patent: Sep. 12, 2006

(54) METHOD AND APPARATUS FOR GENERATION AND SELECTION OF TACHYCARDIA THERAPY HIERARCHY

(75) Inventors: Vinod Sharma, Blaine, MN (US); Paul J. Degroot, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 610 days.

(21) Appl. No.: 10/368,991

(22) Filed: Feb. 20, 2003

(65) Prior Publication Data
US 2004/0167579 A1 Aug. 26, 2004

(51) Int. Cl.
*A61N 1/362* (2006.01)

(52) U.S. Cl. ................. 607/4; 607/9; 607/14
(58) Field of Classification Search ......... 607/4–5, 607/9, 14–15, 25
See application file for complete search history.

(56) References Cited

U.S. PATENT DOCUMENTS

| 5,002,052 A | 3/1991 | Haluska ............... 128/419 PG |
| 5,107,850 A | 4/1992 | Olive .......................... 128/705 |
| 5,193,550 A | 3/1993 | Duffin .......................... 607/60 |
| 5,562,708 A | 10/1996 | Combs et al. ................. 607/4 |
| 5,674,251 A | 10/1997 | Combs et al. ................. 607/4 |
| 5,855,593 A | 1/1999 | Olson et al. .................. 607/9 |
| 6,230,059 B1 | 5/2001 | Duffin ......................... 600/510 |
| 6,272,377 B1 | 8/2001 | Sweeney et al. ............ 600/515 |
| 6,445,949 B1 * | 9/2002 | Kroll ............................. 607/4 |
| 6,456,876 B1 * | 9/2002 | Kroll ............................. 607/4 |
| 2002/0023654 A1 * | 2/2002 | Webb .......................... 128/899 |
| 2003/0023273 A1 * | 1/2003 | DeGroot et al. ............... 607/4 |
| 2004/0073261 A1 * | 4/2004 | Kroll ............................. 607/5 |

FOREIGN PATENT DOCUMENTS

EP 0 518 599 A2 * 6/1992

* cited by examiner

*Primary Examiner*—Carl Layno
(74) *Attorney, Agent, or Firm*—Michael C. Soldner; Girma Wolde-Michael

(57) ABSTRACT

A method and apparatus for generating and selecting therapies, or hierarchies of therapies, that may be used to treat episodes of atrial or ventricular tachycardia. A characteristic of a detected tachycardia event is determined, and a hierarchy of therapies to treat the detected tachycardia event is selected in response to the determined characteristic.

15 Claims, 6 Drawing Sheets

| 200 | 204 | 206 | 208 | 210 |
|---|---|---|---|---|
| | CYCLE LENGTH | MORPHOLOGY | SUCCESS | ACCELERATION |
| 202 → TACHYCARDIA NO. 1 | CYCLE LENGTH NO. 1 | MORPHOLOGY NO. 1 | "A" = 0/4<br>"B" = 25/30<br>"C" = 2/5 | "A" = 0/4<br>"B" = 0/30<br>"C" = 0/5 |
| TACHYCARDIA NO. 2 | CYCLE LENGTH NO. 2 | MORPHOLOGY NO. 2 | "A" = 8/16<br>"B" = 0/5<br>"C" = 4/9 | "A" = 0/16<br>"B" = 5/5<br>"C" = 0/9 |
| TACHYCARDIA NO. 3 | CYCLE LENGTH NO. 3 | MORPHOLOGY NO. 3 | "A" = 0/1<br>"B" = 1/1<br>"C" = 0/0 | "A" = 0/1<br>"B" = 0/1<br>"C" = 0/0 |

FIG. 6

METHOD AND APPARATUS FOR GENERATION AND SELECTION OF TACHYCARDIA THERAPY HIERARCHY

TECHNICAL FIELD

The present invention relates generally to implantable medical devices, and more particularly, the present invention relates to a method and apparatus for providing therapy in response to detected events.

BACKGROUND

Tachycardia is an abnormal heart rhythm characterized by rapid activation of one or more chambers of the heart of a patient. Tachycardia is often qualified by the locus of origin: a tachycardia that originates in the ventricles of the heart is called a ventricular tachycardia (VT) and a tachycardia that originates in the atria of the heart is called an atrial tachycardia (AT) or a supraventricular tachycardia (SVT). Some VTs, if untreated, may accelerate into ventricular fibrillation, in which the pumping ability of the heart is seriously impaired.

In a single patient, two episodes of tachycardia may be different. The causes for these differences could be many, such as disease progression, changes in medication, presence of multiple reentrant circuits and differences in site of origin. Hence, a single patient may experience distinct VTs or ATs over time.

Some tachycardias respond well to medication, and others may be treated with surgery such as radio frequency (RF) ablation. In some patients, VT or AT may respond well to antitachycardia pacing (ATP), in which small electric stimulations from an implantable pulse generator (IPG) in an implantable medical device (IMD) disrupt the propagation of electrical signals that cause the tachycardia. The IMD may be programmed to administer several forms of ATP therapies, and may apply one ATP therapy after another until the tachycardia terminates.

In some circumstances, a tachycardia may fail to terminate in response to ATP, and therefore certain IMDs include the capability of delivering a higher energy cardioversion shock to terminate the tachycardia. In addition, some IMDs may be programmed to administer several cardioversion shocks of progressively increasing energy. Cardioversion therapies tend to be painful compared with ATP therapies, which tend to go unnoticed by the patient. As a result, since ATP therapies may be just as effective for a given episode as cardioversion shock therapies, some patients are treated with one or more ATP therapies prior to being treated with one or more cardioversion therapies in an attempt to avoid the discomfort associated with cardioversion.

SUMMARY

In general, the present invention is directed to therapies, or hierarchies of therapies, that may be used to treat AT or VT. Because a patient can experience several different tachycardias over time, a therapy that may be effective against one tachycardia may not be as effective against another tachycardia. According to the present invention, tachycardia episodes are distinguished from one another according to a tachycardia characteristic, such as morphology, cycle length or a combination of both. Therapies that are historically effective against a tachycardia having a particular morphology, for example, are likely to be effective when a tachycardia with the same morphology recurs.

In one embodiment, the present invention provides techniques for determining a characteristic of a tachycardia and selecting a hierarchy of therapies to treat the tachycardia as a function of the determination. An IMD applying this method ascertains a tachycardia characteristic such as tachycardia morphology, cycle length or other metric, and determines whether a tachycardia having similar characteristics has been previously encountered. If the morphology or cycle length has been previously encountered, the IMD may select a hierarchy in which the therapies that have been most historically effective against the tachycardia having that characteristic are applied first.

In another embodiment, the invention provides techniques for determining a characteristic of a tachycardia, and associating the characteristic with a hierarchy of therapies to treat the tachycardia. If an IMD encounters a tachycardia having a characteristic not previously encountered, the IMD applies a default hierarchy of therapies to the tachycardia, and records which applied therapy successfully terminates the tachycardia. The IMD may associate the tachycardia characteristic with a hierarchy in which the successful therapy is applied first.

The method further provides techniques for updating hierarchies as the IMD accumulates data. A therapy in a hierarchy may be successful on one occasion against tachycardia having a particular characteristic, and may be unsuccessful on another occasion. The IMD keeps track of which therapies are successful and which therapies are unsuccessful, as well as the frequency of success or failure of each therapy. The IMD adjusts the order of therapies in the hierarchy as a result of the performance of the therapies. The IMD may also keep track of therapies that accelerate the tachycardia and make it worse. A therapy that accelerates the tachycardia having a particular characteristic is moved to the end of the hierarchy therapies applied to treat tachycardia with that characteristic, or may be dropped from the hierarchy entirely. The very same therapy may still be a part of a hierarchy used to treat tachycardia having a different characteristic, however.

In other embodiments, the invention is directed to a computer-readable medium containing instructions for carrying out the techniques described above.

In a further embodiment, the present invention is directed to a device that includes at least one electrode to detect electrical activity associated with a tachycardia, and a processor to determine a characteristic of the tachycardia and to select a hierarchy of therapies to treat the tachycardia as a function of the determination. The device includes memory to store the therapies and the hierarchies of therapies. The processor is configured to determine a morphology of the tachycardia by performing a morphological analysis, and to compare the morphology to at least one morphological template. The processor may further be configured to determine that the morphology matches the morphological template when a degree of resemblance between the morphology and the template exceeds a predetermined threshold.

In an additional embodiment, the present invention is directed to a device that includes at least one electrode to detect electrical activity associated with a tachycardia and a processor to determine a characteristic of the tachycardia and to associate the characteristic with a hierarchy of therapies to treat the tachycardia. The device further includes memory to store the characteristic and the hierarchy associated with the characteristic.

The present invention results in one or more advantages, such as improved safety and effectiveness of anti-tachycardia therapies. The patient need not be treated with the same hierarchy of therapies for all tachycardia episodes. Rather, therapies and hierarchies of therapies are customized to a particular patient and to the particular tachycardias to which the patient is susceptible. Therapies are ranked in a hierarchy as a function of historical performance, and therapies with greater effectiveness historically for a given tachycardia may be applied first. As a result, two tachycardia episodes with different characteristics are each terminated promptly.

Because different hierarchies may be applied to distinct tachycardias, a therapy need not be discarded merely because that therapy is unsuccessful in treating a particular tachycardia. The therapy may be included in another hierarchy for treating another tachycardia. In addition, the invention allows each hierarchy to self-improve dynamically. In particular, as more data related to the success or failure of therapies in a hierarchy is collected, the order of the therapies in the hierarchy may change, with more effective therapies being applied first and less effective therapies being applied later. In this way, more effective therapies are applied more frequently and less effective therapies are applied more rarely, or not at all.

In addition, the improved effectiveness of ATP therapies results in more tachycardias being successfully treated with ATP therapies, with less need for cardioversion therapies. More effective use of ATP therapies means that the patient may avoid discomfort associated with cardioversion therapies.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 6 is an exemplary lookup table that illustrates a technique for storing tachycardia characteristics and associated hierarchies of therapies.

DETAILED DESCRIPTION

Figure 1:
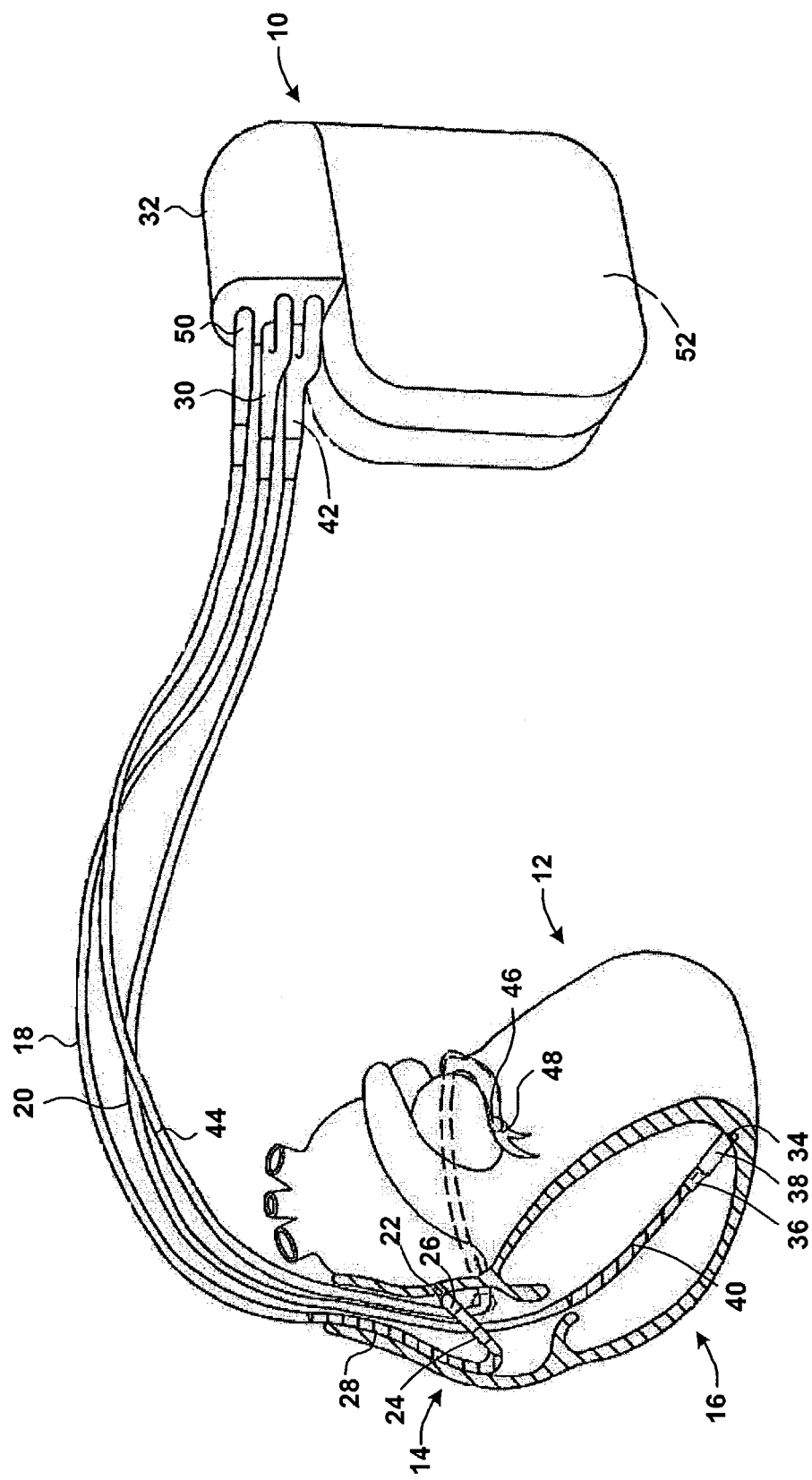
FIG. 1 is a schematic illustration of an atrial and ventricular chamber pacemaker/cardioverter/defibrillator with leads extending to a human heart.

FIG. 1 depicts an exemplary implantable medical device (IMD) 10 that may practice the techniques of the invention. In the example of FIG. 1, IMD 10 is an implantable multi-chamber pacemaker that includes anti-tachycardia pacing (ATP), cardioversion and defibrillation capability. The invention is not limited to the particular IMD shown in FIG. 1, however, but may be practiced by any number of implantable devices. The techniques of the invention may be practiced by a device that paces a single cardiac chamber or several chambers, that paces one or more atria or one or more ventricles, that includes or lacks cardioversion and defibrillation capability, and that paces in any of several pacing modes. The techniques of the invention may be practiced by any device that supplies ATP therapy, or cardioversion therapy, or both.

IMD 10 includes an implantable pulse generator (IPG) (not shown in FIG. 1) that generates pacing stimuli to administer one or more ATP therapies to heart 12. In some circumstances, the IPG may generate pacing stimuli for purposes other than ATP, e.g., to perform antibradycardia pacing. In the embodiment shown in FIG. 1, pacing stimuli are applied to the right atrium 14, for example, or the right ventricle 16, or both. IMD 10 also includes circuitry to sense atrial and ventricular activations, including activations that may be generated during episodes of atrial tachycardia (AT) or ventricular tachycardia (VT). Atrial and ventricular bipolar pace/sense electrode pairs at the distal ends of leads 18 and 20, respectively, carry out the pacing and sensing functions.

In right atrium 14, the distal end of atrial lead 18 includes an extendable helical pace/sense tip electrode 22 and a pace/sense ring electrode 24. Helical electrode 22 extends from electrode head 26 into the atrial appendage. Pace/sense electrodes 22 and 24 are employed for atrial pacing, including delivery of atrial ATP therapies, and for sensing of P-waves indicative of atrial activation. The distal end of atrial lead 18 also includes an elongated coil defibrillation electrode 28 that can deliver a defibrillation shock to right atrium 14. Electrode 28 may also be used to deliver cardioversion therapy to right atrium 14.

Cardioversion therapy typically involves delivery of less energy to heart 12 than defibrillation therapy, but both cardioversion and defibrillation therapies are painful to the patient. ATP therapies, by contrast, involve far less energy than cardioversion and defibrillation therapies. ATP therapies are often well-tolerated by patients, and in some cases, ATP therapies may proceed without the patient becoming aware of the therapies. ATP and cardioversion may both be effective in terminating AT, but when ATP is as effective as cardioversion in terminating AT, ATP may be favored over cardioversion to avoid causing the patient undue discomfort.

Atrial lead 18 includes conductors (not shown) that electrically couple electrodes 22, 24 and 28 to IMD 10. The conductors may be arranged coaxially, coradially, in parallel, or in another configuration, and may be insulated from one another and from the tissue of the patient. The proximal end of atrial lead 18 includes a bifurcated connector 30 that couples the conductors to a connector block 32 on IMD 10.

In right ventricle 16, the distal end of ventricular lead 20 likewise may include a pace/sense tip electrode 34 and a pace/sense ring electrode 36. Pace/sense tip electrode 34 may be a helical electrode that extends from electrode head 38 toward the apex of heart 12. Pace/sense electrodes 34 and 36 are employed for ventricular pacing, including delivery of ventricular ATP therapies, and for sensing of R-waves indicative of ventricular activation. The distal end of ventricular lead 20 also includes an elongated coil defibrillation electrode 40 that can deliver a defibrillation shock or cardioversion therapy to right ventricle 16. As noted above, cardioversion and defibrillation therapies are painful. Ventricular ATP therapies cause considerably less discomfort to the patient, and may be as effective in terminating a given episode of VT as cardioversion.

Like atrial lead 18, ventricular lead 20 includes one or more insulated conductors (not shown) that electrically couple electrodes 34, 36 and 40 to IMD 10. The proximal end of ventricular lead 20 includes a bifurcated connector 42 that couples the conductors to connector block 32.

FIG. 1 illustrates deployment of a coronary sinus lead 44. Coronary sinus lead 44 may include one or more insulated conductors. The proximal end of coronary sinus lead 44 includes one or more electrodes, such as pace/sense electrode 46. Pace/sense electrode 46 may be deployed within the great vein 48 of heart 12, and may be used to deliver pacing therapies, including ATP therapies, to the left side of heart 12. A connector 50 at the proximal end of the coronary sinus lead 44 couples the conductors in lead 44 to connector block 32. In some embodiments of the invention, coronary sinus lead 44 may include an elongated exposed coil wire defibrillation electrode (not shown).

IMD 10 includes a housing 52 that, in some embodiments of the invention, serves as a "can" electrode. In unipolar operation, IMD 10 may deliver an electrical stimulation to heart 12 via an electrode disposed on one or more of leads 18, 20 or 44, with housing 52 being a part of the return current path. In bipolar operation, by contrast, IMD 10 may deliver an electrical stimulation to heart 12 via a tip electrode, with a ring electrode providing the principal return current path.

In the embodiment depicted in FIG. 1, IMD 10 delivers pacing stimuli to right atrium 14 and right ventricle 16 via electrodes 22 and 34, respectively, and senses activations via the same electrodes. The electrodes sense the electrical activity that accompanies AT or VT. The electrodes also deliver one or more ATP therapies to treat AT or VT.

IMD 10 may be programmed to administer more than one ATP therapy. ATP therapies may differ from one another by the manner in which pacing pulses are applied to heart 12 to terminate AT or VT. One ATP therapy, for example, may deliver a sequence of pacing pulses separated from one another by constant time intervals, while another ATP therapy may deliver a sequence of pacing pulses separated from one another by time intervals that shorten with each pulse in the series. The number of pulses in the ATP therapies may vary from one therapy to another. IMD 10 may also be programmed to administer cardioversion therapy at more than one energy level, and may be programmed to deliver cardioversion therapies according to a hierarchy.

The present invention provides techniques for generating a hierarchy of therapies as a function of a tachycardia characteristic. A tachycardia characteristic may include cycle length, i.e., the time interval between activations, or morphology, i.e., the shape of the electrical waveforms that accompany the activations. A tachycardia characteristic may also include a metric that is a function of a plurality of individual tachycardia characteristics. The present invention further provides techniques for selecting a therapy, or hierarchy of therapies, as a function of tachycardia characteristics, as described below.

With these techniques, IMD 10 applies a therapy or a hierarchy of therapies that is likely to treat a particular tachycardia effectively. In general, episodes of tachycardia having similar characteristics are likely to respond to a therapy in the same way. Accordingly, the present invention provides for generation and selection of hierarchies of therapies that have historically been successful in terminating episodes having similar tachycardia characteristics. Techniques for generating a hierarchy of therapies and for selecting a therapy or a hierarchy of therapies will be described in more detail below.

Figure 2:
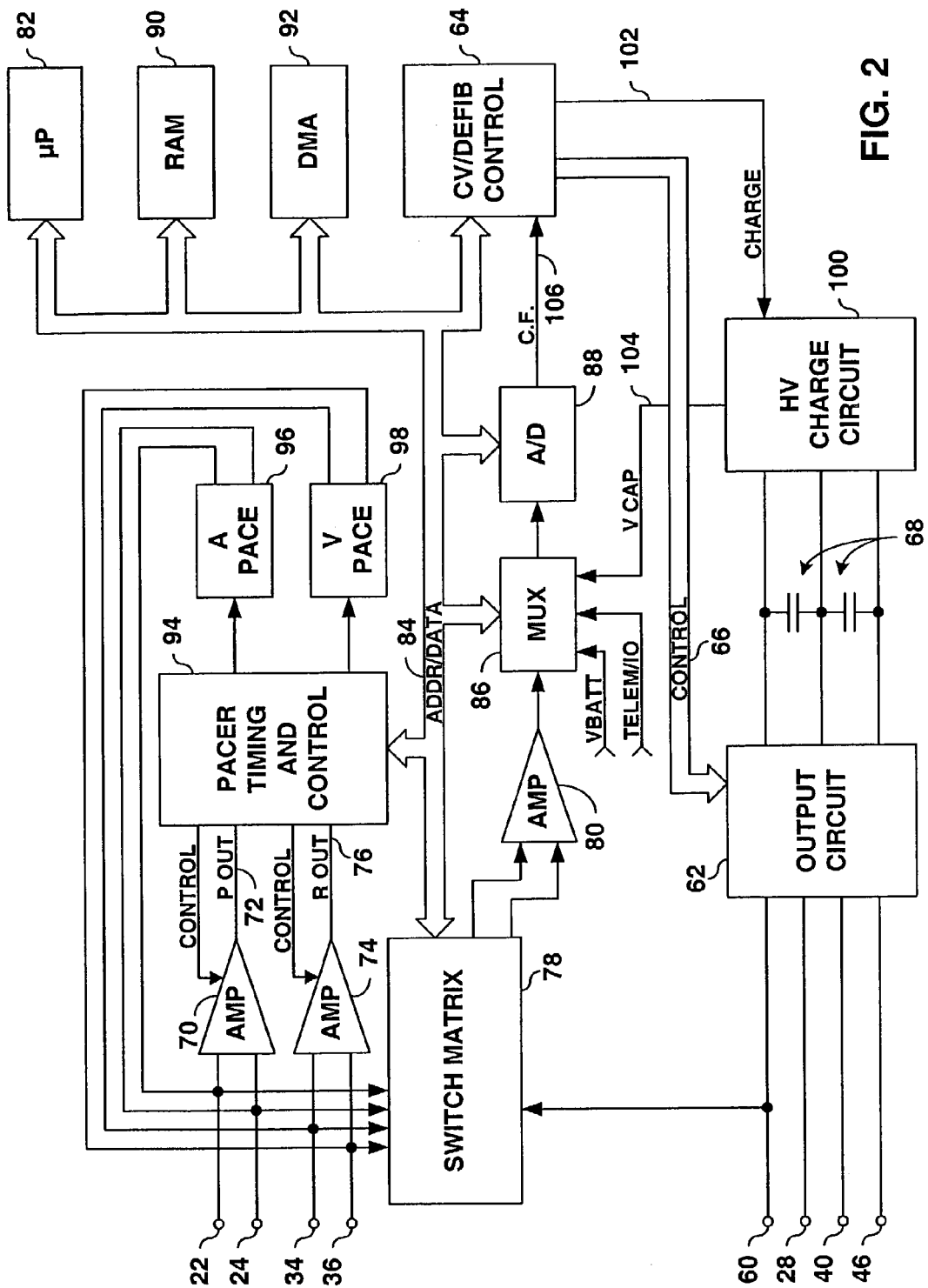
FIG. 2 is a block diagram of the implantable medical device depicted in FIG. 1.

FIG. 2 is a functional schematic diagram of one embodiment of IMD 10 and illustrates how IMD 10 detects episodes of tachycardia and delivers therapies, such as ATP and cardioversion, to address the episodes. This diagram is exemplary of the type of device in which various embodiments of the present invention may be embodied, and the present invention is not limited to the particular schematic shown. On the contrary, the present invention may be practiced in a wide variety of devices, including single- and multi-chamber devices, and implantable devices that do not include cardioversion or defibrillation capability.

FIG. 2 includes electrode terminals 22, 24, 28, 34, 36, 40 and 46, which correspond to the electrodes shown in FIG. 1. Electrode 60 corresponds to the uninsulated portion of housing 52 of IMD 10. Electrodes 28, 40 and 46 are coupled to high voltage output circuit 62, which includes high voltage switches controlled by cardioversion/defibrillation (CV/defib) control logic 64 via control bus 66. Switches disposed within circuit 62 determine which electrodes are employed and which electrodes are coupled to the positive and negative terminals of a capacitor bank 68 during delivery of defibrillation or cardioversion shocks.

Electrodes 22 and 24, located on or in right atrium 14, are coupled to a P-wave amplifier 70. Amplifier 70 may include an automatic gain controlled amplifier providing an adjustable sensing threshold as a function of the measured P-wave amplitude. Amplifier 70 generates a signal on P-out line 72 whenever the signal sensed between electrodes 22 and 24 exceeds the sensing threshold. The time intervals between signals on P-out line 72 reflect the cycle length of atrial activations, and may be indicative of whether the patient is experiencing an episode of AT. In particular, short cycle lengths may be indicative of AT.

Electrodes 34 and 36, located in right ventricle 16, are coupled to an R-wave amplifier 74. Amplifier 74 may include an automatic gain controlled amplifier providing an adjustable sensing threshold as a function of the measured R-wave amplitude. Amplifier 74 generates a signal on R-out line 76 whenever the signal sensed between electrodes 34 and 36 exceeds the sensing threshold of amplifier 74. The time intervals between signals on R-out line 76 reflect the cycle length of ventricular activations and may be indicative of whether the patient is experiencing an episode of VT.

As noted above, cycle length may be one of the tachycardia characteristics that may be associated with a therapy or a hierarchy of therapies. In some patients, it may be possible to distinguish one tachycardia from another by cycle length. In these patients, IMD 10 may be able to implement a power-saving mode. IMD 10 is powered by a self-contained power source such as a battery (not shown in FIGS. 1 and 2). Determining a tachycardia characteristic by determining a cycle length generally consumes less power than determining other tachycardia characteristics, such as morphology. Consequently, the capability of distinguishing one tachycardia from another by cycle length may preserve the battery life of IMD 10.

A switch matrix 78 selects electrodes for coupling to a wide band amplifier 80 for use in digital signal analysis. Selection of electrodes is controlled by microprocessor 82 via data/address bus 84. The signals from the selected electrodes are provided to multiplexer 86, and are thereafter converted to multi-bit digital signals by A/D converter 88. The signals may be stored in random access memory (RAM) 90 under control of direct memory access (DMA) circuit 92.

Digital signal analysis includes, but is not limited to, a morphological analysis of waveforms sensed by the selected electrodes. Morphological analysis may include wavelet analysis, Fourier analysis or similar spectral analysis techniques, but the invention is not limited to those analytical techniques. Microprocessor 82 may employ digital signal analysis techniques to characterize the digitized signals stored in RAM 90 to recognize and classify the patient's heart rhythm or to determine the morphology of the signals employing any of several signal processing methodologies.

Signals sensed via electrodes 22, 24, 34 and 36 are utilized to determine whether to administer cardiac pacing, ATP, cardioversion or defibrillation therapies. Pacer timing/control circuitry 94 receives signals from P-out line 72 and R-out line 76, and computes various timing intervals as a function of the timing of the received signals. Pacer timing/control circuitry 94 also may include programmable digital counters that control pacing according to any of several pacing modes.

Pacer output circuitry 96 and 98, which are coupled to electrodes 22, 24, 34 and 36, generate pacing and ATP stimuli under the control of pacer timing/control circuitry 94. The IPG of IMD 10 includes microprocessor 82, in cooperation with pacer timing/control circuitry 94 and pacer output circuitry 96 and 98.

Pacer timing/control circuitry 94 also computes intervals such as R—R intervals, P—P intervals, P-R intervals and R-P intervals. These intervals may be used to detect the presence of a fast heart rate, which may be an indicator of a tachycardia. A fast heart rate may also be indicative of sinus tachycardia, i.e., a fast heart rate in response to a physiological stimulus, such as exercise. Microprocessor 82 and pacer timing/control circuitry 94 cooperate to apply any of a number of algorithms to discriminate a tachycardia such as VT or AT, for which antitachycardia therapy may be indicated, from sinus tachycardia, for which therapy is not indicated. Microprocessor 82 and pacer timing/control circuitry 94 further cooperate to apply any of a number of algorithms to discriminate a tachycardia such as VT or AT, which may terminate in response to antitachycardia therapies, from other tachyarrhythmias such as atrial fibrillation and ventricular fibrillation, which generally do not respond to antitachycardia therapies. The invention may be practiced with any algorithm or algorithms that detect an atrial or ventricular tachycardia.

When IMD 10 detects an atrial or ventricular tachycardia, microprocessor 82 may select an ATP regimen that includes a plurality of ATP therapies arranged in a hierarchy. In general, the first ATP therapy in a hierarchy is applied initially. If the first ATP therapy fails to terminate the tachycardia, the second ATP therapy in the hierarchy is applied, and so on. RAM 90 may store one or more hierarchies. The hierarchies may be selected for different tachycardia cycle lengths, tachycardia cycle length regularity, or tachycardia waveform morphology.

For each ATP therapy that is applied, microprocessor 82 loads parameters such as timing intervals from RAM 90 into pacer timing/control circuitry 94, which controls delivery of the ATP therapy. Microprocessor 82 evaluates the outcome of the ATP therapy, and determines whether ATP therapy should be discontinued or whether the next therapy in the hierarchy ought to be applied.

In some circumstances, a tachycardia may be unresponsive to all ATP therapies in the selected hierarchy. In some of those circumstances, cardioversion may be indicated. Cardioversion therapies, like ATP therapies, may differ from one another and may be arranged in a hierarchy, with the first cardioversion therapy in the hierarchy applied first, the second cardioversion therapy in the hierarchy applied if the first fails, and so on.

When a cardioversion or defibrillation pulse is required, microprocessor 82 may control the timing, strength and duration of cardioversion and defibrillation pulses. In response to the detection of atrial or ventricular fibrillation or tachycardia requiring a cardioversion pulse, microprocessor 82 activates CV/defib control circuitry 64, which initiates charging of capacitor bank 68 via charging circuit 100, under the control of high voltage charging control line 102. The voltage on the high voltage capacitors is monitored via VCAP line 104, which is passed through multiplexer 86, and in response to reaching a predetermined value set by microprocessor 82, results in generation of a logic signal on Cap Full (CF) line 106 to terminate charging. A defibrillation or cardioversion pulse may be delivered by output circuit 62.

Figure 3:
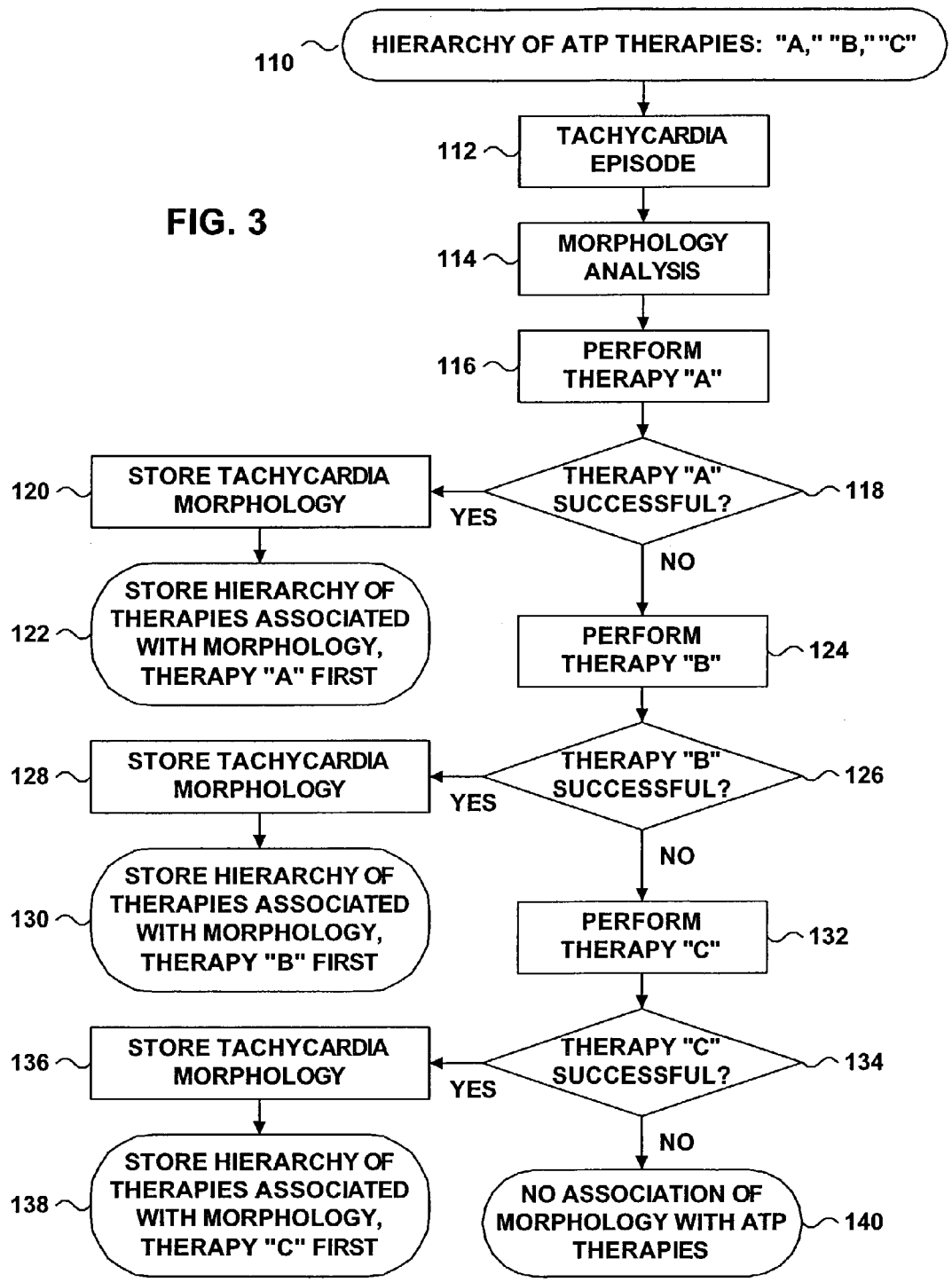
FIG. 3 is a flow diagram illustrating exemplary techniques for associating a therapy hierarchy, such as a set of ATP therapies, with a tachycardia characteristic, such as morphology.

FIG. 3 is a flow diagram illustrating techniques for associating a therapy hierarchy with a tachycardia characteristic. For purposes of illustration, FIG. 3 uses morphology as the tachycardia characteristic and shows generation of a hierarchy of ATP therapies as a function of morphology. The techniques shown in FIG. 3 may be used with AT and VT. The present invention is not limited to use of morphology as a tachycardia characteristic, however, and IMD 10 may employ similar techniques for other tachycardia characteristics, such as cycle length or a metric that is a function of a plurality of tachycardia characteristics. IMD 10 may also employ similar techniques for other therapies, such as cardioversion therapies.

For purposes of illustration, it is assumed that IMD 10 is programmed to support three ATP therapies, identified as "A," "B" and "C." In addition, it is assumed that the pre-selected, default hierarchy for the three therapies calls for therapy "A" to be applied first, then for therapy "B" to be applied should therapy "A" fail to terminate the tachycardia, then for therapy "C" to be applied should therapy "B" fail (110). The therapies, and the hierarchy, are stored in memory 90.

Upon detection of a tachycardia episode (112), IMD 10 performs a morphological analysis on the tachycardia (114). IMD 10 may, for example, capture a waveform sensed via electrodes 34 and 36, convert the waveform to a digital form with A/D converter 88, and determine the morphology of the digital waveform with microprocessor 82. The result of the determination may be a measure of the morphology of the tachycardia waveform, such as a set of frequency components, or a template of the shape of the waveform.

Microprocessor 82 directs ATP according to the default hierarchy. Accordingly, microprocessor 82 loads parameters associated with ATP therapy "A" from RAM 90 into pacer timing/control circuitry 94, and pacer timing/control circuitry 94 delivers ATP therapy "A."

Microprocessor 82 evaluates the outcome of the ATP therapy (118). If therapy "A" is successful, microprocessor 82 stores in memory 90 the result of the morphological determination, such as a template associated with the tachycardia episode (120). Microprocessor 82 also associates a hierarchy of therapies with the stored template (122). Because therapy "A" was successful, therapy "A" is first in the hierarchy. As will be described below, the rank of a therapy in a hierarchy may be a function of the historical performance of the therapies in the hierarchy. Accordingly, associating the stored template with a hierarchy (122) may comprise recording that therapy "A" was attempted one time, and was successful on that single attempt.

If therapy "A" is unsuccessful, microprocessor 82 loads parameters associated with ATP therapy "B" into pacer timing/control circuitry 94, and pacer timing/control circuitry 94 delivers ATP therapy "B" (124). Microprocessor 82 evaluates whether therapy "B" is successful (126), and if so, microprocessor 82 stores the template (128) and associates with the stored template a hierarchy in which therapy "B" is first (130).

Because therapy "A" was attempted and was unsuccessful, therapy "A" may be moved to the last position in the hierarchy. Therapy "A" need not be discarded completely, however. An ATP therapy that fails to terminate an episode of tachycardia having a particular characteristic on one occasion may succeed in terminating an episode of tachycardia having the same characteristic on a later occasion. The converse is also true. An ATP therapy that succeeds in terminating an episode of tachycardia having a particular characteristic on one occasion may fail to terminate an episode of tachycardia having the same characteristic on a later occasion. As will be described below, a therapy hierarchy may be modified as more episodes of tachycardia occur, and as the data concerning the effectiveness of the therapies in the hierarchy accumulates.

If therapy "B" is unsuccessful, microprocessor 82 loads parameters associated with ATP therapy "C" into pacer timing/control circuitry 94, and pacer timing/control circuitry 94 delivers ATP therapy "C" (132). Microprocessor 82 evaluates whether therapy "C" is successful (134), and if so, microprocessor 82 stores the template (136) and associates with the stored template a hierarchy in which therapy "C" is first (138).

Because therapies "A" and "B" were attempted and were unsuccessful, therapies "A" and "B" are moved behind therapy "C" in the hierarchy. It may make no difference at this time whether therapy "A" is ranked higher than therapy "B" in the hierarchy, as both therapies may have been tried one time and both were equally ineffective in terminating the tachycardia. As will be shown below in connection with FIGS. 5 and 6, further experience with therapies "A" and "B" may cause one to be ranked above the other.

In some circumstances, however, it may be important to rank therapy "A" higher than therapy "B," or vice versa. It is possible that a particular therapy not only fails to terminate the tachycardia, but actually accelerates the tachycardia, thereby making the tachycardia worse. A therapy that fails to terminate the tachycardia may be ranked above a therapy that accelerates the tachycardia.

If none of therapies "A," "B" and "C" is successful, then microprocessor 82 does not associate the template with any hierarchy (140). IMD 10 may be programmed to repeat ATP therapies, and may be programmed to repeat the therapies in a different order. In that case, microprocessor 82 loads parameters associated with a previously unsuccessful ATP therapy into pacer timing/control circuitry 94, and pacer timing/control circuitry 94 delivers the ATP therapy again (116). In the event the tachycardia terminates in response to an ATP therapy, then microprocessor 82 may associate the template with a hierarchy (122, 130 or 138). IMD 10 may also be programmed to try cardioversion therapies when ATP therapies fail.

Figure 4:
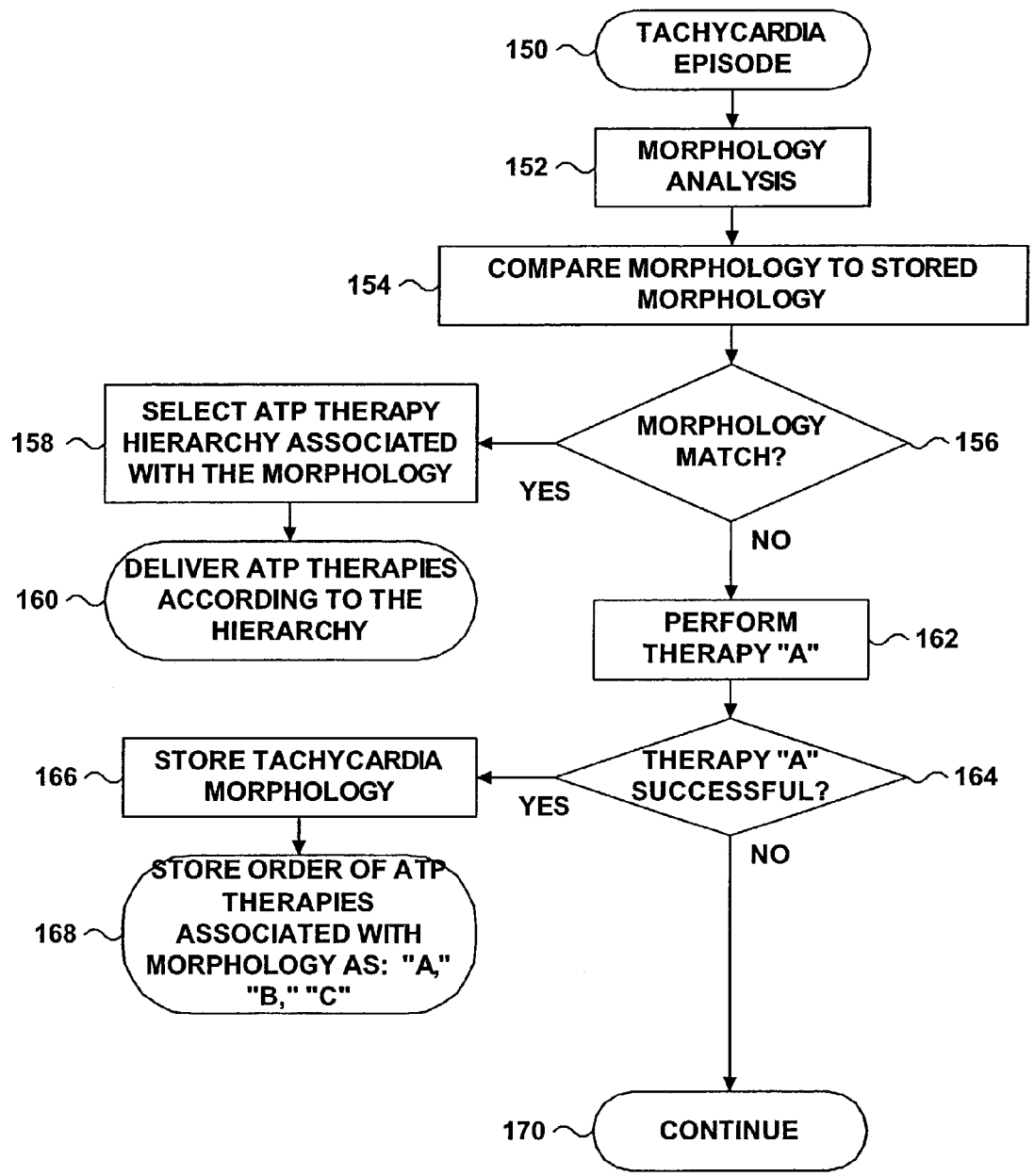
FIG. 4 is a flow diagram illustrating exemplary techniques for selecting a therapy hierarchy, such as a set of ATP therapies, as a function of a tachycardia characteristic, such as morphology.

FIG. 4 is a flow diagram illustrating techniques for selecting a therapy, or a therapy hierarchy, as a function of a tachycardia characteristic. As with FIG. 3, FIG. 4 illustrates the techniques with ATP therapies, using morphology as the tachycardia characteristic. The present invention is not limited to ATP therapies, however, or to use of morphology as a tachycardia characteristic. Similar techniques may be applied to therapies that include cardioversion, and tachycardia characteristics other than morphology.

For purposes of illustration, it is assumed that IMD 10 has already associated at least one tachycardia morphology template with a hierarchy of ATP therapies. Upon detection of a tachycardia episode (150), IMD 10 determines the morphology of the tachycardia (152). IMD 10 compares the morphology of the present tachycardia episode with one or more morphology templates stored in memory 90 (154), to see if the morphology of the present episode is similar to the morphology of at least one previous episode (156).

IMD 10 may practice any technique for comparison and matching (154, 156). For example, microprocessor 82 may compute a degree of resemblance between the morphology of the present tachycardia waveform and the morphology of the stored template. The degree of resemblance may be a mathematical correlation, for example, or any other measure of how closely one shape resembles another. Microprocessor 82 may also determine that a match is present when the degree of resemblance exceeds a predetermined threshold. Ordinarily, the match between a morphology and a template need not be an exact match. Although FIG. 4 depicts a comparison of the present morphology to only one stored template, the comparison may be repeated for other templates that may be stored in memory 90.

When there is a morphology match, IMD 10 selects the hierarchy of ATP therapies that is associated with the matching template (158) and applies therapies according to the selected hierarchy (160). As a result, therapies that have been most historically effective against tachycardia having a particular characteristic are applied first. The desired outcome is that that the tachycardia will terminate sooner with the selected hierarchy than with the default hierarchy. More prompt termination of tachycardia is not guaranteed, but the chances of prompt termination are improved when historical performance of therapies is taken into account.

In the event there is no morphology match, the therapies are applied in the default order. Accordingly, IMD delivers ATP therapy "A" (162) as described above in connection with FIG. 3, evaluates whether therapy "A" is successful (164), and if so, stores the template (166) and associates with the stored template a hierarchy in which therapy "A" is first (168). Otherwise, IMD 10 proceeds to try other therapies as described above in connection with FIG. 3 (170).

Figure 5:
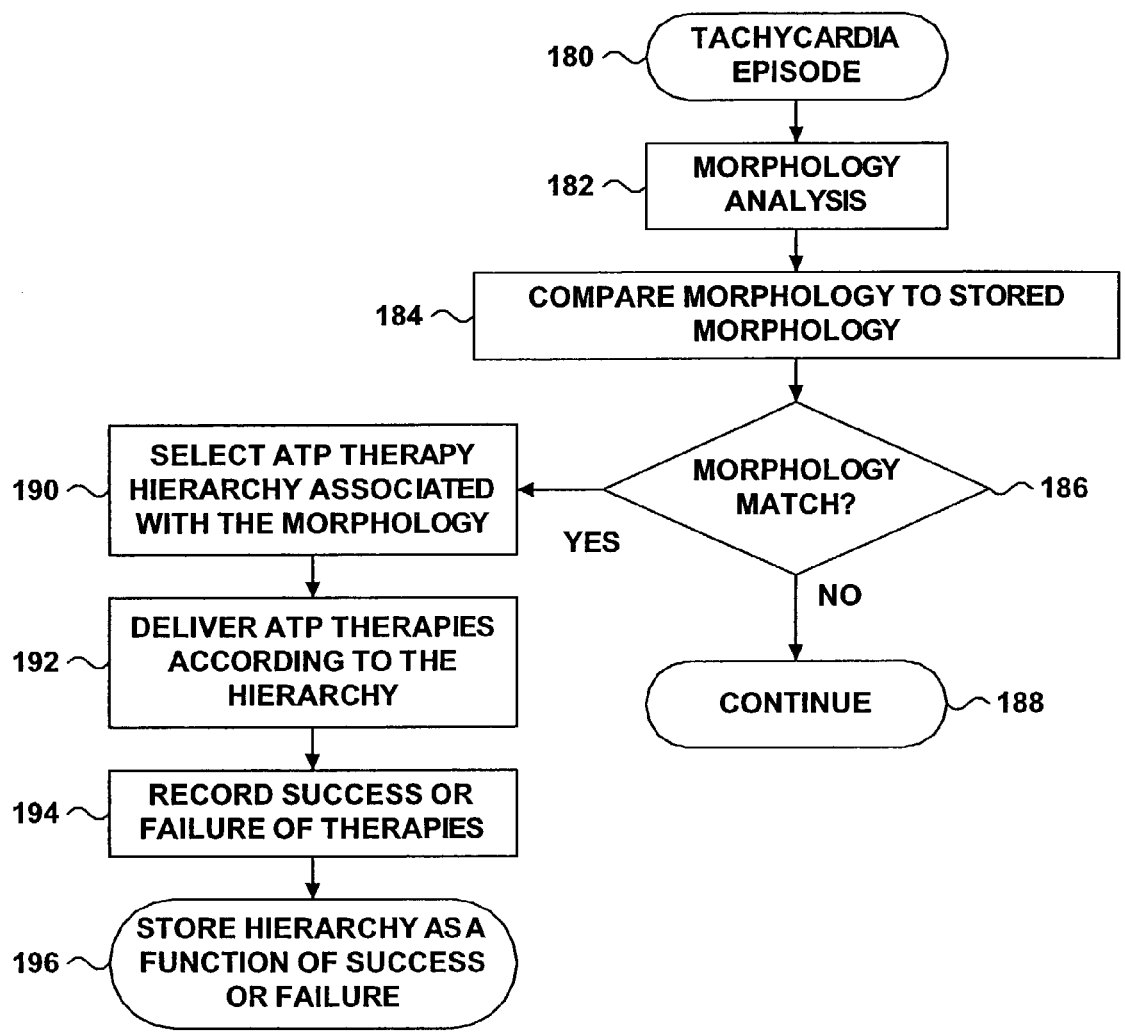
FIG. 5 is a flow diagram illustrating exemplary techniques for changing a therapy hierarchy, such as a set of ATP therapies, as a function of the historical performance of one or more therapies in the hierarchy.

Once a hierarchy is created as a function of the response of the tachycardia to one or more therapies, the hierarchy may be changed as a function of the historical performance of one or more therapies in the hierarchy, as shown in the flow diagram of FIG. 5. As with FIGS. 3 and 4, FIG. 5 illustrates the techniques with ATP therapies and morphology, but the present invention is not limited to ATP therapies or to use of morphology as a tachycardia characteristic. Upon detection of a tachycardia episode (180), IMD 10 performs a morphological analysis on the tachycardia (182), and compares the morphology of the present tachycardia episode with one or more templates stored in memory 90 (184). If there is no match (186), IMD 10 proceeds as shown in FIGS. 3 and 4 (188).

When there is a morphology match, IMD 10 selects the hierarchy of ATP therapies that is associated with the matching template (190), and applies therapies according to the selected hierarchy (192). Although the therapies are applied in an order that has been historically effective against episodes of tachycardia having a particular morphology, there is no guarantee that the therapies will be effective on the present occasion.

IMD 10 records the success or failure of the applied therapies (194) and stores a hierarchy of therapies as a function of the success or failure (196). The stored hierarchy may include the therapies in the same order, or the order of the therapies may be changed. As a result, a hierarchy of therapies may be updated with each recurrence of a tachycardia episode having a particular characteristic, according to the historical performance of the therapies. When the patient experiences a tachycardia episode having the same or a similar characteristic at a later time, the therapy that has been most effective historically will typically be brought to bear soonest, with the hope that the tachycardia will be more promptly terminated.

In some cases, a cardioversion therapy may be more consistently successful in terminating a tachycardia than any of several ATP therapies. Even so, IMD 10 may give preference to ATP therapy over cardioversion therapy, even if the historical success rate of ATP therapy is lower, when ATP therapy provides a reasonable chance of a successful termination of the tachycardia. As a result, the need for painful cardioversion therapies may be reduced. Whether a chance of a successful termination is reasonable may take into consideration the risks of accelerating the tachycardia or of prolonging the episode duration by attempting ATP.

FIG. 6 illustrates a technique for storing tachycardia characteristics and associated hierarchies of therapies in memory 90. The data may be stored in a lookup table 200. Table 200 is an exemplary table that assumes, for purposes of illustration, that three different tachycardias 202 have been identified as occurring in a patient. The three tachycardias are identified for convenience as "Tachycardia No. 1," "Tachycardia No. 2" and "Tachycardia No. 3." Associated with each tachycardia are one or more tachycardia characteristics. In table 200, cycle length 204 and morphology 206 are the stored tachycardia characteristics.

In some patients, one tachycardia event may be distinguished from another by a single tachycardia characteristic, such as cycle length. In other patients, however, it may be useful to determine more than one tachycardia characteristic when selecting a hierarchy. It may be possible that "Tachycardia No. 1" and "Tachycardia No. 2" both have similar cycle length, for example. When the patient experiences an episode with approximately the same cycle length, it may be helpful to determine the morphology of a tachycardia before classifying the tachycardia as "Tachycardia No. 1," "Tachycardia No. 2" or another tachycardia not previously observed. In some embodiments of the invention, a tachycardia characteristic may be a metric that is a function of one or more tachycardia characteristics.

In addition, associated with the tachycardia characteristic are antitachycardia therapies. Once again, it is assumed for purposes of illustration that the medical device is programmed to apply three ATP therapies, identified as "A," "B" and "C." Table 200 records the number of successful therapies 208, as well as the number of instances in which a therapy accelerated the tachycardia 210.

Table 200 shows that the patient has had therapy delivered for the tachycardia labeled "Tachycardia No. 1" thirty-nine times. Therapy "A" has been applied four times, but has not succeeded in terminating any tachycardia that has the tachycardia characteristics of "Tachycardia No. 1." Therapy "B" has been applied thirty times, with a success rate of about eighty-three percent. Therapy "C" has been applied five times, with a success rate of forty percent. None of the therapies resulted in acceleration.

Should the patient experience another tachycardia episode having a tachycardia characteristic that matches "Tachycardia No. 1," then the hierarchy of therapies will be "B" followed by "C" followed by "A." The historical effectiveness of each therapy determines the hierarchy, with the therapy having the highest historical effectiveness generally being applied first. As noted above, IMD 10 may give preference to ATP therapy over cardioversion therapy; even if the historical success rate of ATP therapy as lower than the historical success rate of cardioversion therapy.

Table 200 shows that the patient has had therapy delivered for the tachycardia labeled "Tachycardia No. 2" thirty times. Therapy "A" has the highest historical effectiveness against "Tachycardia No. 2," and therapy "C" has the second highest historical effectiveness. Therapy "B" has been applied five times, but has not succeeded in terminating the episode, and on each occasion resulted in acceleration.

Should the patient experience another tachycardia episode having a tachycardia characteristic that matches "Tachycardia No. 2," then the hierarchy of therapies will be "A" followed by "C." Once again, the historical effectiveness of each therapy generally determines the hierarchy. Therapy "B," which has never been effective against "Tachycardia No. 2" and which has a history of making the tachycardia worse, may be discontinued as a therapy for "Tachycardia No. 2." Although therapy "B" may still be available to treat "Tachycardia No. 1" and "Tachycardia No. 3," therapy "B" may be dropped from the hierarchy used to treat "Tachycardia No. 2." In this way, IMD 10 may use historical performance as a basis for discontinuing ineffective therapies or therapies that accelerate the tachycardia. In some circumstances, discontinuation of ineffective therapies may cause a hierarchy of therapies to include a single therapy.

Table 200 further shows that the patient has had therapy delivered for the tachycardia labeled "Tachycardia No. 3" twice. According to the techniques shown in FIG. 3, therapy "A" was applied but was ineffective. Therapy "B" was applied and succeeded in terminating the episode. Therapy "C" has not yet been applied against "Tachycardia No. 3." Should the patient experience another tachycardia episode having a tachycardia characteristic that matches "Tachycardia No. 3," then the hierarchy of therapies may be "B" followed by "C" followed by "A." Although not shown in table 200, the effectiveness of cardioversion therapies may also be recorded, and a hierarchy of cardioversion therapies may be determined by the historical effectiveness of the therapies. It may be possible that ATP therapies may be historically ineffective in terminating a tachycardia having a particular characteristic, but cardioversion is highly effective in terminating the tachycardia. In those circumstances, IMD 10 may bypass ineffective ATP therapies and proceed to cardioversion directly. Although ATP therapies may be attempted before resort is made to cardioversion to avoid patient discomfort, the historical ineffectiveness of ATP therapies may cause ATP therapies to be disregarded when such therapies are ineffective.

According to the present invention, therapies and hierarchies of therapies may be customized to a particular patient and to the tachycardias to which the patient is susceptible. The patient need not be treated with the same hierarchy of therapies for all tachycardia episodes. A patient that experiences two distinct VTs, for example, may receive two distinct therapy regimens. As a result, the most historically effective therapies will be more promptly applied to each VT, with the hope that each tachycardia will be more promptly terminated.

In addition, therapies that are unsuccessful in treating tachycardia having a particular characteristic, or that accelerate the tachycardia, may be retained for treating another tachycardia having another characteristic. The present invention allows one hierarchy to include a therapy that is historically successful against a tachycardia having one characteristic, and another hierarchy to omit the same therapy against a tachycardia having another characteristic.

The present invention further provides for self-improving hierarchies. As more data are collected about the success or failure of therapies in a hierarchy, the order of the therapies in the hierarchy may change. Therapies that are more effective may be applied first. Therapies that accelerate the tachycardia may be applied rarely, or may be dropped from the hierarchy entirely.

These advantages combine for improved safety and effectiveness of anti-tachycardia therapies. Application of the techniques of the invention to ATP therapies may make such therapies more effective, thereby reducing the need for painful cardioversion therapies. Reduction of the need for cardioversion therapies entails the added advantage of saving power and preserving the battery life of IMD 10.

The preceding specific embodiments are illustrative of the practice of the invention. Various modifications may be made without departing from the scope of the claims. For example, the techniques described above illustrate determining characteristics of a tachycardia such as cycle length or morphology. Other characteristics of a tachycardia, such as metrics reflecting suddenness of onset of the episode or rapidly declining arterial pressure and/or cerebral perfusion, may be considered instead of, or in addition to, cycle length or morphology. Moreover, a hierarchy may be associated with more than one tachycardia characteristic, and more than one tachycardia characteristic may be determined when selecting a hierarchy.

In addition, the order of therapies in a hierarchy need not be solely a function of historical performance. IMD 10 may record whether a therapy has been successful on recent occasions, and may change a hierarchy when a therapy demonstrates a decrease in efficacy. In some cases, the response of the patient to therapy may change, due to factors such as a change in medications or drug dosages. As a result of the change, a therapy with a good historical performance may become less effective or ineffective. Accordingly, IMD 10 may record the recent performance of a therapy. IMD 10 may, for example, record whether a therapy has been unsuccessful for a number of times in a row or whether the success rate of the therapy in the recent short term is significantly below the success rate in the long term. A therapy that demonstrates a marked decrease in efficacy may be moved lower in a hierarchy despite the long-term historical performance of the therapy. Similarly, a therapy that demonstrates a marked improvement in efficacy may be moved higher in hierarchy despite the long-term historical performance of the therapy. In some cases, the changes in the patient's responses to therapy may be so acute that IMD 10 may discard the hierarchies entirely, and use the techniques shown in FIGS. 3, 4 and 5 to develop hierarchies anew.

Some of the techniques described above may be embodied as a computer-readable medium including instructions for a programmable processor such as microprocessor 82 or pacer timing/control circuitry 94 shown in FIG. 2. The programmable processor may include one or more individual processors, which may act independently or in concert. A "computer-readable medium" includes but is not limited to read-only memory, Flash memory and a magnetic or optical storage medium. The medium may include instructions for causing a programmable processor to determine a tachycardia characteristic, such as morphology or cycle length, and to associate the characteristic with a hierarchy of therapies to treat the tachycardia, such as a hierarchy of ATP therapies or cardioversion therapies. The medium may also include instructions for causing a programmable processor to select a hierarchy of therapies to treat the tachycardia as a function of the determination.

These and other embodiments are within the scope of the following claims.

We claim:

1. A method for providing therapy in an implantable medical device, comprising:
   detecting a tachycardia event;
   determining a characteristic of the detected tachycardia event;
   selecting a hierarchy of therapies to treat the detected tachycardia event in response to the determined characteristic;
   applying a therapy corresponding to the selected hierarchy of therapies;
   determining whether the applied therapy terminates the detected tachycardia event;
   storing historical effectiveness of the applied therapy; and
   updating the selected hierarchy of therapies in response to the stored historical effectiveness.

2. The method of claim 1, wherein the characteristic includes at least one of a cycle length of the tachycardia, a morphology of the tachycardia, a metric of suddenness of onset of the tachycardia, a metric of decline of arterial pressure and a metric of decline of cerebral perfusion.

3. The method of claim 1, wherein the therapies in the hierarchy include one of anti-tachycardia pacing therapies and cardioversion therapies.

4. The method of claim 1, further comprising determining whether the applied therapy accelerates the tachycardia event.

5. The method of claim 1, wherein the hierarchy of therapies corresponds to a single therapy.

6. A method for providing therapy in an implantable medical device, comprising:
   detecting a tachycardia event;
   determining a characteristic of the detected tachycardia event; and
   selecting a hierarchy of therapies to treat the detected tachycardia event in response to the determined characteristic, wherein determining the characteristic of the tachycardia event comprises:
   comparing the characteristic to a corresponding characteristic template;
   computing a degree of resemblance between the characteristic and the corresponding characteristic template; and
   determining that the characteristic matches the corresponding characteristic template in response to the degree of resemblance exceeding a predetermined threshold, and wherein selecting a hierarchy of therapies comprises selecting a hierarchy associated with the corresponding characteristic template in response to determining that the characteristic matches the corresponding characteristic template.

7. The method of claim 6, wherein determining the characteristic of the tachycardia event comprises
   determining that the characteristic does not match the corresponding characteristic template in response to the degree of resemblance being less than or equal to a predetermined threshold, and wherein selecting a hierarchy of therapies comprises selecting a default hierarchy in response to determining that the characteristic does not match the corresponding characteristic template.

8. An implantable medical device, comprising:
   a plurality of electrodes detecting a tachycardia event;
   a processor determining a characteristic of the detected tachycardia event and selecting a hierarchy of therapies to treat the detected tachycardia event in response to the determined characteristic; and a storage device, wherein the processor applies a therapy, via the plurality of electrodes, corresponding to the selected hierarchy of therapies, determines whether the applied therapy terminates the detected tachycardia event, stores historical effectiveness of the applied therapy in the storage device, and updates the selected hierarchy of therapies in response to the stored historical effectiveness.

9. The implantable medical device of claim 8, wherein the characteristic includes at least one of a cycle length of the tachycardia, a morphology of the tachycardia, a metric of suddenness of onset of the tachycardia, a metric of decline of arterial pressure and a metric of decline of cerebral perfusion.

10. The implantable medial device of claim 8, wherein the therapies in the hierarchy include one of anti-tachycardia pacing therapies and cardioversion therapies.

11. The implantable medical device of claim 8, wherein the processor determines whether the applied therapy accelerates the tachycardia event.

12. The implantable medical device of claim 8, wherein the hierarchy of therapies corresponds to a single therapy.

13. An implantable medical device, comprising:
a plurality of electrodes detecting a tachycardia event; and
a processor determining a characteristic of the detected tachycardia event and selecting a hierarchy of therapies to treat the detected tachycardia event in response to the determined characteristic, wherein the processor compares the characteristic to a corresponding characteristic template, computes a degree of resemblance between the characteristic and the corresponding characteristic template, and determines that the characteristic matches the corresponding characteristic template in response to the degree of resemblance exceeding a predetermined threshold, and wherein the processor selects a hierarchy associated with the corresponding characteristic template in response to determining that the characteristic matches the corresponding characteristic template.

14. The implantable medical device of claim 13, wherein the processor determines that the characteristic does not match the corresponding characteristic template in response to the degree of resemblance being less than or equal to a predetermined threshold, and wherein the processor selects a default hierarchy in response to determining that the characteristic does not match the corresponding characteristic template.

15. A computer-readable medium comprising instructions for causing a programmable processor to:
detect a tachycardia event;
determine a characteristic of the detected tachycardia event;
select a hierarchy of therapies to treat the detected tachycardia event in response to the determined characteristic;
apply a therapy corresponding to the selected hierarchy of therapies;
determine whether the applied therapy terminates the detected tachycardia event;
store historical effectiveness of the applied therapy; and
update the selected hierarchy of therapies in response to the stored historical effectiveness.

* * * * *